United States Patent
Hu et al.

(10) Patent No.: US 7,780,979 B2
(45) Date of Patent: Aug. 24, 2010

(54) FABRIC-SUPPORTED CHITOSAN MODIFIED TEMPERATURE RESPONSIVE PNIPAAM/PU HYDROGEL AND THE USE THEREOF IN PREPARATION OF FACIAL MASK

(75) Inventors: Jinlian Hu, Hong Kong (CN); Wenguang Liu, Hong Kong (CN); Baohua Liu, Hong Kong (CN)

(73) Assignee: The Hong Kong Polytechnic University, Hong Kong (CN)

( * ) Notice: Subject to any disclaimer, the term of this patent is extended or adjusted under 35 U.S.C. 154(b) by 1150 days.

(21) Appl. No.: 11/341,762

(22) Filed: Jan. 27, 2006

(65) Prior Publication Data

US 2006/0286152 A1 Dec. 21, 2006

(30) Foreign Application Priority Data

Jun. 21, 2005 (CN) ........................ 2005 1 0200341

(51) Int. Cl.
*A61F 13/00* (2006.01)
*A61F 15/00* (2006.01)
*A61K 9/62* (2006.01)

(52) U.S. Cl. .................. 424/443; 424/445; 424/461; 424/402; 602/45; 602/48; 602/49; 442/97

(58) Field of Classification Search ................ 424/443, 424/445, 461, 402; 442/97
See application file for complete search history.

(56) References Cited

U.S. PATENT DOCUMENTS

| | | | |
|---|---|---|---|
| 5,420,118 A | 5/1995 | Alban et al. | |
| 6,761,896 B1 | 7/2004 | Znaiden et al. | |
| 2005/0260409 A1* | 11/2005 | Payne et al. | 428/364 |
| 2006/0128241 A1* | 6/2006 | Tseng | 442/85 |

FOREIGN PATENT DOCUMENTS

CN 2462923 12/2001

OTHER PUBLICATIONS

K.C. Gupta, K. Khandekar, Temperature-responsive cellulose by Ceric(IV) ion-initiated graft copolymerization of n-isopropylacrylamide, Biomacromolecules 2003, 4:758-765.
A. Chilkoti, M.R. Dreher, D.E. Meyer, D. Raucher, Targeted drug delivery by thermally responsive polymers, Advanced Drug Delivery Reviews 2002, 54: 613-630.
C. K. Han, Y. H. Bae, Inverse Thermally-reversible gelation of aqueous N-isopropylacrylamide copolymer solution, Polymer 1998, 39:2809-2814.
J. O. Karlsson, P. Gatenholm, Solid-supported wettable hydrogels prepared by ozone induced grafting, Polymer 37:4251-4256, 1996.
Z. T. Zhang, L. Chen, J. M. Ji, Y. I, Huang, D. H. Chen, Antibacterial Properties of cotton fabrics treated with chitosan, Textile Research Journal, 2003, 73: 1103-1106.

* cited by examiner

*Primary Examiner*—Lynda Salvatore
(74) *Attorney, Agent, or Firm*—Workman Nydegger

(57) ABSTRACT

This invention involves fabric-supported chitosan modified temperature responsive PNIPAAm/PU hydrogel and the use thereof in preparation of facial mask. The merit of this invention is the hydrogel formed can reversibly swell and deswell near body temperature; the incorporation of PU can suppress the syneresis of PNIPAAm at an elevated temperature; Grafting of PNIPAAm and PU onto the surface of cellulose fabrics can enhance the mechanical strength of hydrogel; Coupling of chitosan to the surface of hydrogel can not only improve the handle and skin affinity, but also render the facial mask antibacterial; The hydrogel is capable of loading a variety of nutrients (or other functional components), which can release at body temperature; the hydrogel facial mask can be reusable with repeated rinsing.

15 Claims, No Drawings

FABRIC-SUPPORTED CHITOSAN MODIFIED TEMPERATURE RESPONSIVE PNIPAAM/PU HYDROGEL AND THE USE THEREOF IN PREPARATION OF FACIAL MASK

TECHNICAL FIELD

The present invention relates to fabric-supported chitosan modified temperature responsive PNIPAAm/PU hydrogel and the use thereof in preparation of facial mask.

BACKGROUND OF THE INVENTION

Polymer hydrogels are crosslinked (physical or chemical) three-dimensional networks, which is capable of absorbing solvents and swelling to a limited degree without dissolution. They behave like sort of solid and liquid. If under external stimuli such as temperature, pH, ionic strength, chemicals, pressure, light and electric field, a reversible change of shape and volume to hydrogels, they are called environment sensitive polymer gels or smart gels. Apart from hydrophilicity, hydrogels has a good permeability allowing water and oxygen to pass through. Furthermore, the hydrogels with suitable crosslinking density are tender and elastic, resembling soft tissue. Thus, hydrogels are widely applied as contact lens, tissue engineering scaffolds, artificial muscle, drug delivery carriers and wound dressings. Recently, considerable attention is being paid to developing hydrogel facial masks. A skin-care facial mask made from polyacrylic acid copolymer was reported. The compositions provide improved skin feel and residue characteristics together with excellent moisturizing, emolliency, rub-in and absorption characteristics (U.S. Pat. No. 5,420,118/1993). In Chinese Patent (CN 2462923), the preparation method of a reusable hydrogel skin-care patch was reported. It was composed of back membrane, hydrogel and protecting layer. The hydrogel layer can be loaded with a variety of nutrients for skin beauty. A poly(hydroxycarboxylic acid) hydrogel-based cosmetic patch was publicized in (U.S. Pat. No. 6,761,896/2004). The novel patch comprise of static magnetic layer and hydrogel layer encapsulating nutrients. The magnetic patch aids in reducing facial wrinkles and transdermal ingredient delivery.

The hydrogel-based facial masks developed to date are insensitive to surrounding stimuli. The nutrients loaded are delivered in a passive mode, and the weak mechanical strength inherent to hydrogel leaves much to be desired. It is noted that most of hydrogels applied as facial masks are devoid of antibacterial activity and have a poor skin affinity.

Poly(N-isopropylacrylamide, PNIPAAm) is a special polymer with a low critical solution temperature (LCST). While temperature is below 32-34°, PNIPAAm is dissolved in water; above this temperature, PNIPAAm precipitate in water. (K. C. Gupta, K. Khandekar, Temperature-responsive cellulose by Ceric(IV) ion-initiated graft copolymerization of N-isopropylacrylamide, Biomacromolecules 2003, 4:758-765). For crosslinked PNIPAAm hydrogel, it occurs to shrink at above LCST; while below LCST, it becomes swollen. The water absorbency and releasing rate of drug loaded can be tuned by varying temperature. This characteristic has been applied to temperature responsive drug delivery system and separation membrane. (A. Chilkoti, M. R. Dreher, D. E. Meyer, D. Raucher, Targeted drug delivery by thermally responsive polymers, Advanced Drug Delivery Reviews 2002, 54: 613-630). However, a heavy syneresis occurs to PNIAAm at above LCST, which is undesirable in facial mask. (C. K. Han, Y. H. Bae, Inverse thermally-reversible gelation of aqueous N-isopropylacrylamide copolymer solution, Polymer 1998, 39:2809-2814). Polyurethane (PU) hydrogel is known to be biocompatible, and exhibit sort of elasticity and high swelling degree. Much research has demonstrated that grafting hydrogel onto the surface of textile can raise the mechanical strength of gel itself. (J. O. Karlsson, P. Gatenholm, Solid-supported wettable hydrogels prepared by ozone induced grafting, Polymer 37: 4251-4256.).

As a naturally occurring basic polysaccharide, chitosan is biocompatible, non-toxic, and antibacterial. It was also shown to have a good skin affinity, cause no allergy and readily form membrane. (Z. T. Zhang, L. Chen, J. M. Ji, Y. L, Huang, D. H. Chen, Antibacterial properties of cotton fabrics treated with Chitosan, Textile Research Journal, 2003, 73:1103-1106). In view of the characteristics above, this invention aims to develop cellulose fabric-supported chitosan modified thermoresponsive NIPAAm/Polyurethane copolymer hydrogel for facial mask. The hydrogel layer can load a variety of nutrients such as vitamins, aloe extract. At body temperature, the hydrogel deswell to facilitate the release of nutrients and water.

SUMMARY OF THE INVENTION

This invention relates to fabric-supported chitosan modified temperature responsive Poly(N-isoproplacrylamide)/Polyurethane (PNIPAAm/PU) hydrogel and the use thereof in preparation of facial mask. The hydrogel obtained feels tender and soft without obvious syneresis; it rapidly respond to the change of temperature and the response temperature varies from 32 to 35°; the ingredients loaded in hydrogel layer are released slowly at body temperature; the incorporation of chitosan renders the facial mask antibacterial.

In one aspect, the invention provides fabric-supported temperature responsive PNIPAAm/PU hydrogel (crosslinked-PNIPAAm/PU hydrogel grafted nonwoven fabric) which is prepared with the following materials:

| | |
|---|---|
| Vinyl-capped PU anionomer (VPUA) | 0.2-2 parts by weight |
| Triethylamine | 0.05-0.1 parts by weight |
| NIPAAm | 1-10 parts by weight |
| Methylenebisacrylamide(MBAA) | 0.01-2 parts by weight |
| Initiator | 0.001-0.02 parts by weight |
| Promoter | 0.001-0.01 parts by weight |
| Nonwoven fabric | 0.02-0.1 parts by weight |
| Deionized water | 10-50 parts by weight |

In another aspect, the invention provides fabric-supported chitosan modified temperature responsive PNIPAAm/PU hydrogel which is prepared by the two kinds of surface modification ways of above mentioned fabric-supported temperature responsive PNIPAAm/PU hydrogel with chitosan. Fabric-supported chitosan modified temperature responsive PNIPAAm/PU hydrogel according to the invention may be prepared with the following materials:

| | |
|---|---|
| crosslinked-PNIPAAm/PU hydrogel grafted nonwoven fabric | 0.1-10 parts by weight |
| Carbodiimide(EDC) | 0.02-0.5 parts by weight |
| Chitosan | 0.05-1 parts by weight |
| pH 4-5 buffer | 10-50 parts by weight |

Alternative chitosan modification method was static adsorption. The carboxylic groups in the PU chains are negative and the amidocyanogen in the chitosan are positive.

These two opposite charged groups can adsorb each other when meet. The materials used are followed.

| | |
|---|---|
| crosslinked-PNIPAAm/PU hydrogel grafted nonwoven fabric | 0.1-10 parts by weight |
| Chitosan | 0.05-1 parts by weight |
| pH 4-5 buffer | 10-50 parts by weight |

In further another aspect, the invention provides use of fabric-supported chitosan modified temperature responsive PNIPAAm/PU hydrogel in preparation of facial mask.

DETAILED DESCRIPTION OF THE INVENTION

One aspect of the invention provides fabric-supported temperature responsive PNIPAAm/PU hydrogel (crosslinked-PNIPAAm/PU hydrogel grafted nonwoven fabric) which is prepared with the following materials:

| | |
|---|---|
| Vinyl-capped PU anionomer (VPUA) | 0.2-2 parts by weight |
| Triethylamine | 0.05-0.1 parts by weight |
| NIPAAm | 1-10 parts by weight |
| Methylenebisacrylamide(MBAA) | 0.01-2 parts by weight |
| Initiator | 0.001-0.02 parts by weight |
| Promoter | 0.001-0.01 parts by weight |
| Nonwoven fabric | 0.02-0.1 parts by weight |
| Deionized water | 10-50 parts by weight |

The ratio of PU to NIPAAm by weight is preferably in the range of 1:1 to 1:7; the amount of MBAA is preferably 5-15 wt % of NIPAAm. The said initiator may be one used commonly in the art such as azobisisobutyronitril etc., and preferably is ammonium persulfate. In addition to the use of a initiator, the reaction may be initiated by a processing method commonly used in the art, such as plasma radiation, etc. The said promoter may be one used commonly in the art, and preferably is N,N,N',N'-tetra-methylethylene-diamine.

VPUA used in Fabric-supported temperature responsive PNIPAAm/PU hydrogen according to the invention may be prepared with the following materials:

| | |
|---|---|
| Polyether diol | 10-60 parts by weight |
| Carboxyl containing diol | 3-20 parts by weight |
| aliphatic diisocyanate | 12-30 part by weight |
| hydroxyalkyl acrylate | 5-11 parts by weight |
| solvent | 50-200 parts by weight |

Preferably, the content of carboxyl-containing diol is 5-15 parts by weight.

Another aspect of the invention provides fabric-supported chitosan modified temperature responsive PNIPAAm/PU hydrogel which is prepared by the modification of above mentioned fabric-supported temperature responsive PNIPAAm/PU hydrogel with chitosan. Fabric-supported chitosan modified temperature responsive PNIPAAm/PU hydrogel according to the invention may be prepared with the following materials:

| | |
|---|---|
| crosslinked-PNIPAAm/PU hydrogel grafted nonwoven fabric | 0.1-10 parts by weight |
| Carbodiimide(EDC) | 0.02-0.5 parts by weight |
| Chitosan | 0.05-1 parts by weight |
| pH 4-5 buffer | 10-50 parts by weight |

Preferably, the molecular weight of chitosan is in the range of 5000-50,000.

Fabric-supported chitosan modified temperature responsive PNIPAAm/PU hydrogel according to the invention is a kind of new material for preparing facial mask. The preparing method thereof mainly includes the following steps: preparation of Vinyl-capped PU anionomer (VPUA); VPUA, NIPAAm and methylenebisacrylamide were copolymerized on the surface of cellulose nonwoven fabrics; The fabric supported slightly crosslinked hydrogel was further modified with chitosan.

(1) Isocyanate-capped prepolymer was prepared from the mixture of 10-60 parts by weight of polyether diol, 3-20 parts by weight of carboxyl containing diol and 12-30 parts by weight of aliphatic diisocyanate in 50-200 parts by weight of solvent with continuous $N_2$ purging at 80° C.;

(2) 5-11 parts by weight of hydroxyalkyl acrylate was added into the above prepolymer, and the reaction was kept for 5 h at 60-70° C. to generate the vinyl containing anionic urethane macromonomer (APUA).

(3) 0.2-2 parts by weight of APUA was placed into a three-necked flask, into which 0.05-0.1 parts by weight of triethylamine was added. After thoroughly stirring, 10-50 parts by weight of deionized water was added dropwise. The transparent PU solution was mixed with 1-10 parts by weight of NIPAAm and 0.01-2 parts by weight of MBAA, followed with addition of 0.001-0.02 parts by weight of initiator and 0.001-0.01 parts by weight of promoter. Then the mixture was transferred into a flat-bottomed flask containing 0.02-0.1 parts by weight of nonwoven fabric with N2 bubbling for 30 min. The reactants were sealed and left at room temperature for 8 h.

(4) The fabric-supported PNIPAAM/PU hydrogel was repeatedly washed with water to remove unreacted monomers and impurities. Then, the hydrogel was immersed in water at room temperature for 48-64 h with water being replaced at 3-6 h intervals.

0.1-10 parts by weight of purified hydrogel was immersed in a buffer (pH4-5) containing 0.02-0.5 parts by weight of EDC. After treatment for 1 h, 0.05-1 parts by weight of chitosan was added, and the reaction was left at room temperature for 24 h. The final nonwoven supported chitosan modified PNIPAAm/PU hydrogel was rinsed in the same way aforementioned.

In this invention, the contents of carboxyl groups in PU, the feeding ratio of NIPAAm to PU, the amount of crosslinker and chitosan molecular weight are variable in a broad range. To realize the purpose of this invention, the content of carboxyl-containing diol is preferably 5-15 parts by weight. Preferably, the ratio of PU to NIPAAm is in the range of 1:1 to 1:5. The amount of MBAA is preferably 5-15 wt % of NIPAAm; preferably, the molecular weight of chitosan is in the range of 5000-50,000.

In further another aspect, the invention provides use of fabric-supported chitosan modified temperature responsive PNIPAAm/PU hydrogel in preparation of facial mask. Compared to the hydrogel facial mask currently applied, the nonwoven fabric-supported chitosan modified PNIPAAm/PU hydrogel facial mask according to the invention is characterized by:

(1) Temperature sensitive PNIPAAm was copolymerized with waterborne anionic polyurethane. The gel reversibly swelled and shrank near body temperature. The incorporation of PU suppressed the heavy syneresis of PNIPAAm at an elevated temperature.

(2) The mechanical strength of hydrogel was improved by grafting PNIPAAm and PU onto the surface of nonwoven fabric.

(3) Chitosan, a natural polysaccharide was coupled to the surface of hydrogel, which improved skin affinity and sense of comfort, and imparted antibacterial activity to the mask. The transition temperature remained unchanged after introducing chitosan.

(4) Due to its suitable thickness, the gel layer could load a variety of nutrients whose release was facilitated with water molecules at body temperature.

(5) The facial mask is reusable. After use, it can be purified by alternately immersing in hot and cold water several times. The purified mask can reabsorb different nutrients based on individual's likes and dislikes or be used without loading any ingredients.

Several Points Need to be Emphasized:

(1) The polyether diols in this invention need to be dehydrated, NIPAAm and MBAA are purified by recrystallization, and chitosan is dialyzed to remove impurities.

(2) The transition temperature of hydrogel on the surface of fabric is measured on differential scanning calorimeter. 8-15 mg of wet sample is hermetically placed into an aluminum pan. Heating scans were recorded on a Perkin Elmer DSC 7 calorimeter from 20 to 50° C. at scan rate of 5.0° C./min, and deionised water was used as a reference.

(3) The antibacterial rate (AR) is evaluated with colony counting method:

$$AR=(N_1-N_2)/N_2$$

Where, $N_1$ and $N_2$ are the numbers of bacteria after and before culture with facial mask. The bacteria species for assaying are *E. coli* and *S. aureus*.

(4) To characterize the temperature sensitive delivery behavior of nutrients loaded in hydrogel, vitamin C is used as a model ingredient. Due to its instability in air, sodium thiosulphate was added to stabilize vitamin C in solution. The concentration of Vc released was determined on a UV-Vis spectrophotometer. The maximum wavelength is 264 nm.

Example 1

10 g of polyoxytetramethylene glycol (PTMG, Mn=1000) diol, 3.13 g of 2,2-dimethylol propionic acid (DMPA) and 50 g of dimethylformamide (DMF) were placed into a four-necked flask equipped with a stirrer, a thermometer and a reflux condenser. The mixture was stirred for 15 min with continuous nitrogen purging, and 11.12 g of IPDI was added. The reaction was kept at 80° for 4 h, and cooled down to 60-70°. Then 4.77 g of 2-Hydroxyethyl methacrylate was added. The reaction proceeded for 5 h to yield a colorless or shallow yellowish viscous liquid of vinyl-capped anionic polyurethane macromonomer (VPUA).

0.5 g of VPUA was placed into a four-necked flask, followed by addition of 0.25 of triethylamine with intense agitation for 5 min. 60 g of deionized water was added dropwise, and stirred for 10 min. Then 2.5 g of NIPAAm and 0.2 g of MBAA was dissolved in this mixture, into which 0.05 g of ammonium persulfate (APS) and 0.03 g of N,N,N',N'-tetramethyl ethylene diamine (TEMED) were added. After a homogenous solution was formed, it was transferred into a flat-bottomed flask containing 200 mg of nonwoven fabric with N2 bubbling for 20 min. The reactants were sealed and left at room temperature for 8 h.

The fabric-supported PNIPAAM/PU hydrogel was repeatedly washed with water to remove unreacted monomers and impurities. Then, the hydrogel was immersed in water at room temperature for 24 h with water being replaced at 4 h intervals.

The purified hydrogel was immersed in 10 g of HCl/TEMED buffer (pH4.7) containing 50 mg of EDC. After treatment for 1 h, 1 g of HCl/TEMED (pH4.7) solution containing 1 wt % chitosan (Mn=10,000, degree of deacetylation is 80%) was added, and the reaction was left at room temperature for 24 h. The final nonwoven supported chitosan modified PNIPAAm/PU hydrogel was rinsed in the same way aforementioned.

The LCST of fabric-supported hydrogel was determined as 33.2° on an Elmer Perkin DSC-7 calorimeter.

Antibacterial assessment: *E. coli*. and *S. aureus* were separatively inoculated in a nutrient broth (peptone, 10 g; beef extract, 3 g; NaCl, 3 g in 1000 mL distilled water, pH 7.0) and incubated in a shaking bed (130 rpm) at 37° C. for 24 h. The culture solution was further diluted, and the concentration of bacteria was determined with colony counting on a microscope. The concentration of *E. Coli* and *S. aureus* is $1.2\times10^3$/ml and $1.2\times10^5$/ml, respectively. Then 10 ml of bacterium solution was placed onto the surface of hydrogel facial mask; the control is 10 ml of bacterium solution in the absence of hydrogel. The bacteria were cultured in incubator at 37° for 24 h, and the growth of bacteria was checked on a microscope. The resulting AR is 70%.

Temperature sensitive release behavior of Vc: 0.01 g of Vc was dissolved in 100 ml aqueous solution of 0.04% sodium thiosulphate, into which fabric-supported chitosan modified PNIPAAm/PU hydrogel was immersed for 1 h. The surface of hydrogel was rinsed with 0.04% sodium thiosulphate to remove Vc adsorbed on the surface. The hydrogel samples encapsulated Vc were immersed into 0.04% $NaS_2O_3$ solution at 20 and 37°, respectively. The concentration of Vc in solution was measured at each 5 min interval, and continuously traced for 4 h.

From the concentration of Vc, it was found that within initial 1 h, the releasing rate at 37° was increased 2-3 times compared to that at 20° due to the high temperature-induced shrinkage. At later stage, most of Vc has been released, and the release rate at 37° began to decrease, merely two times as that at 20°.

Example 2

0.8 g of VPUA prepared in Example 1 was placed into a four-necked flask, followed by addition of 0.3 of triethylamine with intense agitation for 5 min. 60 g of deionized water was added dropwise, and stirred for 10 min. Then 2.5 g of NIPAAm and 0.2 g of MBAA was dissolved in this mixture, into which 0.05 g of ammonium persulfate (APS) and 0.03 g of N,N,N',N'-tetramethyl ethylene diamine (TEMED) were added. After a homogenous solution was formed, it was transferred into a flat-bottomed flask containing 200 mg of nonwoven fabric with N2 bubbling for 20 min. The reactants were sealed and left at room temperature for 8 h.

The fabric-supported PNIPAAM/PU hydrogel was repeatedly washed with water to remove unreacted monomers and impurities. Then, the hydrogel was immersed in water at room temperature for 48 h with water being replaced at 3-5 h intervals.

The purified hydrogel was immersed in 10 g of HCl/TEMED buffer (pH4.7) containing 50 mg of EDC. After treatment for 1 h, 1 g of HCl/TEMED (pH4.7) solution containing 1 wt % chitosan (Mn=10,000, degree of deacetylation is 80%) was added, and the reaction was left at room temperature for 24 h. The final nonwoven supported chitosan modified PNIPAAm/PU hydrogel was rinsed in the same way aforementioned.

The LCST of fabric-supported hydrogel was determined as 34.5° C. on an Elmer Perkin DSC-7 calorimeter.

According to the antibacterial assessment method mentioned in Example 1, AR of the facial mask was determined as 75%.

The releasing rate of Vc from hydrogel was measured in terms of method described in Example 1. Within initial 1 h, the releasing rate at 37° was increased 2 times compared to that at 20° due to the high temperature-induced shrinkage. At later stage, most of Vc has been released, and the release rate at 37° began to decrease, merely two times as that at 20°.

Example 3

0.8 g of VPUA prepared in Example 1 was placed into a four-necked flask, followed by addition of 0.3 of triethylamine with intense agitation for 5 min. 60 g of deionized water was added dropwise, and stirred for 10 min. Then 2.5 g of NIPAAm and 0.2 g of MBAA was dissolved in this mixture, into which 0.05 g of ammonium persulfate (APS) and 0.03 g of N,N,N',N'-tetramethyl ethylene diamine (TEMED) were added. After a homogenous solution was formed, it was transferred into a flat-bottomed flask containing 200 mg of nonwoven fabric with N2 bubbling for 20 min. The reactants were sealed and left at room temperature for 8 h.

The fabric-supported PNIPAAM/PU hydrogel was repeatedly washed with water to remove unreacted monomers and impurities. Then, the hydrogel was immersed in water at room temperature for 64 h with water being replaced at 3-5 h intervals.

The purified hydrogel was immersed in 10 g of HCl/TEMED buffer (pH4.7) containing 50 mg of EDC. After treatment for 1 h, 1 g of HCl/TEMED (pH4.7) solution containing 1 wt % chitosan (Mn=5000, degree of deacetylation is 85%) was added, and the reaction was left at room temperature for 24 h. The final nonwoven supported chitosan modified PNIPAAm/PU hydrogel was rinsed in the same way aforementioned.

The LCST of fabric-supported hydrogel was determined as 33.0° on an Elmer Perkin DSC-7 calorimeter.

According to the antibacterial assessment method mentioned in Example 1, AR of the facial mask was determined as 80%.

The releasing rate of Vc from hydrogel was measured in terms of method described in Example 1. Within initial 1 h, the releasing rate at 37° C. was increased 2-3 times compared to that at 20° due to the high temperature-induced shrinkage. At later stage, most of Vc has been released, and the release rate at 37° began to decrease, merely two times as that at 20°.

Example 4

10 g of polyoxytetramethylene glycol (PTMG, Mn=1000) diol, 5.0 g of 2,2-dimethylol propionic acid (DMPA) and 50 g of dimethylformamide (DMF) were placed into a four-necked flask equipped with a stirrer, a thermometer and a reflux condenser. The mixture was stirred for 15 min with continuous nitrogen purging, and 14.0 g of IPDI was added. The reaction was kept at 80° for 4 h, and cooled down to 60-70°. Then 4.77 g of 2-Hydroxyethyl methacrylate was added. The reaction proceeded for 5 h to yield a colorless or shallow yellowish viscous liquid of vinyl-capped anionic polyurethane macromonomer (VPUA).

0.5 g of VPUA prepared in Example was placed into a four-necked flask, followed by addition of 0.3 of triethylamine with intense agitation for 5 min. 60 g of deionized water was added dropwise, and stirred for 10 min. Then 2.5 g of NIPAAm and 0.2 g of MBAA was dissolved in this mixture, into which 0.05 g of ammonium persulfate (APS) and 0.03 g of N,N,N',N'-tetramethyl ethylene diamine (TEMED) were added. After a homogenous solution was formed, it was transferred into a flat-bottomed flask containing 200 mg of nonwoven fabric with N2 bubbling for 20 min. The reactants were sealed and left at room temperature for 8 h.

The fabric-supported PNIPAAM/PU hydrogel was repeatedly washed with water to remove unreacted monomers and impurities. Then, the hydrogel was immersed in water at room temperature for 64 h with water being replaced at 3-6 h intervals.

The purified hydrogel was immersed in 10 g of HCl/TEMED buffer (pH4.7) containing 50 mg of EDC. After treatment for 1 h, 1 g of HCl/TEMED (pH4.7) solution containing 1 wt % chitosan (Mn=10,000, degree of deacetylation is 80%) was added, and the reaction was left at room temperature for 24 h. The final nonwoven supported chitosan modified PNIPAAm/PU hydrogel was rinsed in the same way aforementioned.

The LCST of fabric-supported hydrogel was determined as 35.2° on an Elmer Perkin DSC-7 calorimeter.

According to the antibacterial assessment method mentioned in Example 1, AR of the facial mask was determined as 83%.

The releasing rate of Vc from hydrogel was measured in terms of method described in Example 1. Within initial 1 h, the releasing rate at 37° was increased 1-3 times compared to that at 20° due to the high temperature-induced shrinkage. At later stage, most of Vc has been released, and the release rate at 37° began to decrease, merely 1.5 times as that at 20°.

Example 5

10 g of polyoxytetramethylene glycol (PTMG, Mn=1000) diol, 3.13 g of 2,2-dimethylol propionic acid (DMPA) and 50 g of dimethylformamide (DMF) were placed into a four-necked flask equipped with a stirrer, a thermometer and a reflux condenser. The mixture was stirred for 15 min with continuous nitrogen purging, and 11.12 g of IPDI was added. The reaction was kept at 80° for 4 h, and cooled down to 60-70°. Then 4.77 g of 2-Hydroxyethyl methacrylate was added. The reaction proceeded for 5 h to yield a colorless or shallow yellowish viscous liquid of vinyl-capped anionic polyurethane macromonomer (VPUA).

0.5 g of VPUA prepared in Example was placed into a four-necked flask, followed by addition of 0.25 of triethylamine with intense agitation for 5 min. 60 g of deionized water was added dropwise, and stirred for 10 min. Then 2.5 g of NIPAAm and 0.5 g of MBAA was dissolved in this mixture, into which 0.05 g of ammonium persulfate (APS) and 0.03 g of N,N,N',N'-tetramethyl ethylene diamine (TEMED) were added. After a homogenous solution was formed, it was transferred into a flat-bottomed flask containing 200 mg of nonwoven fabric with N2 bubbling for 20 min. The reactants were sealed and left at room temperature for 8 h.

The fabric-supported PNIPAAM/PU hydrogel was repeatedly washed with water to remove unreacted monomers and impurities. Then, the hydrogel was immersed in water at room temperature for 48 h with water being replaced at 3-5 h intervals.

The purified hydrogel was immersed in 10 g of HCl/TEMED buffer (pH4.7) containing 50 mg of EDC. After treatment for 1 h, 1 g of HCl/TEMED (pH4.7) solution containing 1 wt % chitosan (Mn=10,000, degree of deacetylation is 80%) was added, and the reaction was left at room temperature for 24 h. The final nonwoven supported chitosan modified PNIPAAm/PU hydrogel was rinsed in the same way aforementioned.

The LCST of fabric-supported hydrogel was determined as 33.2° on an Elmer Perkin DSC-7 calorimeter.

According to the antibacterial assessment method mentioned in Example 1, AR of the facial mask was determined as 86%.

The releasing rate of Vc from hydrogel was measured in terms of method described in Example 1. Within initial 1 h, the releasing rate at 37° was increased 3 times compared to that at 20° due to the high temperature-induced shrinkage. At later stage, most of Vc has been released, and the release rate at 37° began to decrease, merely 1.8 times as that at 20°.

Example 6

0.8 g of VPUA prepared in Example 1 was placed into a four-necked flask, followed by addition of 0.3 of triethylamine with intense agitation for 5 min. 60 g of deionized water was added dropwise, and stirred for 10 min. Then 2.5 g of NIPAAm and 0.2 g of MBAA was dissolved in this mixture, into which 0.05 g of ammonium persulfate (APS) and 0.03 g of N,N,N',N'-tetramethyl ethylene diamine (TEMED) were added. After a homogenous solution was formed, it was transferred into a flat-bottomed flask containing 200 mg of nonwoven fabric with N2 bubbling for 20 min. The reactants were sealed and left at room temperature for 8 h.

The fabric-supported PNIPAAM/PU hydrogel was repeatedly washed with water to remove unreacted monomers and impurities. Then, the hydrogel was immersed in water at room temperature for 24 h with water being replaced at 4 h intervals.

The purified hydrogel was immersed in 10 g of HCl/TEMED buffer (pH4.7) containing 1 wt % chitosan (Mn=5000, degree of deacetylation is 85, then the reaction was left at room temperature for 24 h. The final nonwoven supported chitosan modified PNIPAAm/PU hydrogel was rinsed in the same way aforementioned.

The LCST of fabric-supported hydrogel was determined as 33.0° on an Elmer Perkin DSC-7 calorimeter.

According to the antibacterial assessment method mentioned in Example 1, AR of the facial mask was determined as 85%.

The releasing rate of Vc from hydrogel was measured in terms of method described in Example 1. Within initial 1 h, the releasing rate at 37° was increased 2-3 times compared to that at 20° due to the high temperature-induced shrinkage. At later stage, most of Vc has been released, and the release rate at 37° began to decrease, merely two times as that at 20°.

What is claimed is:

1. Fabric-supported temperature responsive poly(N-isopropylacrylamide)polyurethane (PNIPAAm/PU) hydrogel, wherein the said fabric-supported temperature responsive PNIPAAm/PU hydrogel is prepared with the following materials:

| | |
|---|---|
| VPUA | 0.2-2 parts by weight |
| Triethylamine | 0.05-0.1 parts by weight |
| NIPAAm | 1-10 parts by weight |
| Methylenebisacrylamide(MBAA) | 0.01-2 parts by weight |
| Initiator | 0.001-0.02 parts by weight |
| Promoter | 0.001-0.01 parts by weight |
| Nonwoven fabric | 0.02-0.1 parts by weight |
| Deionized water | 10-50 parts by weight. |

2. Fabric-supported temperature responsive poly(N-isopropylacrylamide)polyurethane (PNIPAAm/PU) hydrogel of claim 1, wherein the ratio of PU to NIPAAm by weight is in the range of 1:1 to 1:7.

3. Fabric-supported temperature responsive poly(N-isopropylacrylamide)polyurethane (PNIPAAm/PU) hydrogel of claim 2, wherein the amount of MBAA is 5-15 wt % of NIPAAm.

4. Fabric-supported temperature responsive poly(N-isopropylacrylamide)polyurethane (PNIPAAm/PU) hydrogel of claim 3, wherein the said initiator is ammonium persulfate.

5. Fabric-supported temperature responsive poly(N-isopropylacrylamide)polyurethane (PNIPAAm/PU) hydrogel of claim 4, wherein the said promoter is N,N,N',N'-tetra-methylethylene-diamine.

6. Fabric-supported temperature responsive poly(N-isopropylacrylamide)polyurethane (PNIPAAm/PU) hydrogel of claim 1, wherein said VPUA is prepared with the following materials:

| | |
|---|---|
| Polyether diol | 10-60 parts by weight |
| Carboxyl containing diol | 3-20 parts by weight |
| aliphatic diisocyanate | 12-30 parts by weight |
| hydroxyalkyl acrylate | 5-11 parts by weight |
| solvent | 50-200 parts by weight. |

7. Fabric-supported temperature responsive poly(N-isopropylacrylamide)polyurethane (PNIPAAm/PU) hydrogel of claim 6, wherein the content of carboxyl-containing diol is 5-15 parts by weight.

8. Fabric-supported temperature responsive poly(N-isopropylacrylamide)polyurethane (PNIPAAm/PU) hydrogel of claim 7, wherein the ratio of PU to NIPAAm by weight is in the range of 1:1 to 1:7.

9. Fabric-supported temperature responsive poly(N-isopropylacrylamide)polyurethane (PNIPAAm/PU) hydrogel of claim 8, wherein the amount of MBAA is 5-15 wt % of NIPAAm.

10. Fabric-supported temperature responsive poly(N-isopropylacrylamide)polyurethane (PNIPAAm/PU) hydrogel of claim 9, wherein the said initiator is ammonium persulfate.

11. Fabric-supported temperature responsive poly(N-isopropylacrylamide)polyurethane (PNIPAAm/PU) hydrogel of claim 10, wherein the said promoter is N,N,N',N'-tetra-methylethylene-diamine.

12. Fabric-supported chitosan modified temperature responsive poly(N-isopropylacrylamide)polyurethane (PNIPAAm/PU) hydrogel, wherein the said fabric-supported chitosan modified temperature responsive PNIPAAm/PU hydrogel is prepared by the modification of fabric-supported temperature responsive PNIPAAm/PU hydrogel of anyone of claims 1-11 with chitosan.

13. Fabric-supported chitosan modified temperature responsive poly(N-isopropylacrylamide)polyurethane (PNIPAAm/PU) hydrogel of claim 12, wherein the said fabric-supported chitosan modified temperature responsive PNIPAAm/PU hydrogel is prepared with the following materials:

| | |
|---|---|
| Fabric-supported temperature responsive PNIPAAm/PU hydrogel | 0.1-10 parts by weight |
| Carbodiimide(EDC) | 0.02-0.5 parts by weight |
| Chitosan | 0.05-1 parts by weight |
| pH4-5 buffer | 10-50 parts by weight. |

14. Fabric-supported chitosan modified temperature responsive poly(N-isopropylacrylamide)polyurethane (PNIPAAm/PU) hydrogel of claim 12, wherein the molecular weight of chitosan is in the range of 5000-50,000.

15. Use of Fabric-supported chitosan modified temperature responsive poly(N-isopropylacrylamide)polyurethane (PNIPAAm/PU) hydrogel of claim 12 in preparation of facial mask.

* * * * *